United States Patent [19]

Christ et al.

[11] 4,354,035

[45] Oct. 12, 1982

[54] PROCESS FOR ISOLATING ROSMARINIC ACID FROM PLANTS

[75] Inventors: Bruno Christ, Cologne; Kurt Kesselring, Köttingen, both of Fed. Rep. of Germany

[73] Assignee: A. Nattermann & Cie GmbH, Cologne, Fed. Rep. of Germany

[21] Appl. No.: 242,657

[22] Filed: Mar. 11, 1981

[30] Foreign Application Priority Data

Mar. 15, 1980 [DE] Fed. Rep. of Germany ....... 3010040

[51] Int. Cl.³ ............................................. C07C 69/76
[52] U.S. Cl. ..................................................... 560/75
[58] Field of Search .......................................... 560/75

[56] References Cited

PUBLICATIONS

Chem. Abstract, vol. 53, 19955d, (1958).
Chem. Abstract, vol. 55, 8764b, 1960.

Primary Examiner—Paul J. Killos
Attorney, Agent, or Firm—Pearne, Gordon, Sessions, McCoy & Granger

[57] ABSTRACT

The present invention is related to a new process for producing rosmarinic acid by extraction of certain plants, and in particular of plants of balmmint (*Melissa officinalis*).

3 Claims, No Drawings

PROCESS FOR ISOLATING ROSMARINIC ACID FROM PLANTS

The present invention is related to a new process for producing rosmarinic acid by extraction of certain plants, and in particular of plants of balmmint (*Melissa officinalis*).

The presence of rosmarinic acid (i.e. 3.4-dihydroxy-alpha-[[3-(3.4-dihydroxyphenyl)-1-oxo-2-propenyl]-oxy]-phenylpropionic acid) in various plant species has been proven. Rosmarinic acid is valuable in view of its anti-inflammatory properties (see f.i. German patent application No. P 29 52 114.0).

It is therefor an object of the present invention to provide a new and simple process for isolating rosmarinic acid from certain plants with improved yields and with an improved purity of the final product.

The processes for isolating rosmarinic acid known up to now have the disadvantage of comprising many burdensome steps. For instance, Scarpati and Oriente, Ricera Sci 1958, vol. 28, p. 2392 to 2393 and Tetrahedron 1958, vol. 4, p. 43 to 48 isolated rosmarinic acid from *Rosmarinus officinalis* and Chicory (*Cichorium intybus*) by extraction with water. However, before it is possible to isolate rosmarinic acid by extraction from the aqueous extracts, they have to be subjected to reaction with a lead salt and the resulting precipitated lead salt has to be decomposed by reaction with hydrogen sulfide. According to Gestirner and Schiemenz, Sci. Pharm. 1969, vol. 37, p. 40 to 47, it is necessary at first to remove fat from the drug by extracting the drug with petrolether followed by several further extraction steps. The rosmarinic acid containing fraction is obtainable only after chromatography on a polyamide. In the process of K. Hiller, Pharmazie 1965, vol. 20, p. 574 to 579, the drug at first has to be degreased in the same manner.

It now has surprisingly been found that rosmarinic acid may be obtained in a simple manner in high purity and with high yields when starting from the plants of balmint, i.e. Melissa officinalis. When starting from the ground plant material of balmmint such as leaves, roots, stems, blossoms or seeds, in particular the leaves of balmmint, it is not necessary to degrease them before extraction. The ground plant material is extracted 1 to 3 times with the 10 to 30, preferably with the 20 fold amount of water, i.e. 1 kg of ground plant material is extracted 1 to 3 times with 10 to 30, preferably 20 kg of water, at 80° to 100° C. for 30 to 60 minutes each times, with stirring.

The combined extracts are then acidified by the addition of an inorganic acid, preferably hydrochloric acid, until a pH of 2 to 2.5 is reached and the precipitated by-products are filtered off, for instance by centrifugation or filtration. The extracts cleared from the insolubles are extracted with an alkyl ether such as diethylether, diisopropylether or dipropylether, with a higher alkanol immiscible with water such as n-butanol or isobutanol, or with an ester of an aliphatic carboxylic acid such as ethylacetate. The amount of solvent used for extraction is choosen such that it varies between 1/10 and 3 times the volume of the aqueous phase to be extracted. Preferably, diethylether or diisopropylether are used as solvent for extraction.

The solvent is removed and the resulting residue is stirred with water for 20 to 40 minutes at 40° to 80° C., preferably at 50° to 60° C. Resinous material is separated from the resulting solution which is thereafter stored at 2° to 8° C. After storage for about 4 to 14 hours, possibly precipitated further resinous materials are separated and the solution is evaporated in a vacuum to about one third of its volume and this solution is stored at 2° to 8° C. Rosmarinic acid crystallizes after storage for a certain period of time. This product may be further purified by another recrystallization. F.p.: 171° to 173° C. The crystallization from the above solution may be enhanced by adding seed crystals or rosmarinic acid.

The present process is further illustrated by the following examples without however limiting the same thereto.

EXAMPLE 1

100 g. of ground leaves of balmmint (rosmarinic acid content: 2.1%) are extracted twice with 2 liters of water each time, at 80° to 100° C. for 45 minutes with stirring. The pH of the combined extracts is rendered to a value of 2 to 2.5 by the addition of 25% hydrochloric acid thereto. The precipitated by-products are separated by centrifugation and the resulting solution is extracted 3 times by shaking with diisopropylether. Per each 100 ml. of extract there are used 30 ml. of the organic solvent. During this step about 80% of the starting amount of rosmarinic acid are extracted. The combined organic phases are dried over anhydrous $CaCl_2$, filtrated and evaporated to dryness by means of a rotating evaporator at a bath temperature of about 50° C.

The dry residue (2.7 g.) contains about 54% or 1.45 g. of rosmarinic acid. The product is finely ground and introduced into 75 ml. of water at 50° to 60° C. with vivid stirring. The aqueous mixture is stirred for 30 minutes and filtered through a folded filter. The filtrate is stored for 12 hours at about +4° C., decanted from small amounts of resinous material which separated on the bottom of the container during storage. The resulting solution is evaporated to a volume of 25 ml. After the addition of several seed crystals of rosmarinic acid, the solution is allowed to stand at +4° C. The resulting crystals are filtered off with suction through a filter crucible type 1 D 3, the collected crystals are washed with a few ml. of ice-cold water and thereafter dried in a vacuum. The mother liquor is evaporated to a volume of about 10 m. by means of a rotating evaporator, seeded with crystals of rosmarinic acid and stored at about +4° C. Another small amount of rosmarinic acid crystals separate upon storage for several days. The collected crystals are combined with the first collected product. The crude rosmarinic acid (1.35 g.) is dissolved in 60 ml. of water of about 50° C., a spatula tip full of activated carbon is added to the warm solution and the solution filtered through a folded filter. The filter is washed with 5 ml. of hot water. After the addition of several seed crystals of rosmarinic acid, the desired compound crystallizes upon standing at +4° C. for 2 days. The separated rosmarinic acid crystals are filtered off through a glass filter, washed with a small amount of ice-cold water and dried in a vacuum.

Yield: 1.15 g. (55% of the theoretical).

EXAMPLE 2

100 g. of ground leaves of balmmint are extracted as described in example 1 and the extracts are acidified to a pH of 2–2.5. The acid aqueous solution is extracted with shaking 3 times with diethylether. There are used 30 ml. of ether per each 100 ml. of aqueous phase. The combined organic phases are dried over anhydrous CaCl$_2$, filtered and evaporated to dryness by means of a rotating evaporator with a bath temperature of about +40° C.

The dry residue (4.8 g. containing 32%=1.54 g. of rosmarinic acid) is finely ground and added with stirring to about 90 ml. of water at about 50° C. Stirring is continued for another 30 minutes and the solution is separated from the precipitated resinous material by filtration. The solution is allowed to stand at about +4° C. for 12 hours and the clear solution is decanted from further precipitated resinous material. The resulting solution is evaporated to a volume of about 10 ml. by means of a rotating evaporator and is poured over a column having a diameter of about 3 cm. and a lenghth of about 40 cm. and containing 65 g. of Syphadex LH-20 in 70% aqueous methanol. Elution is carried out with 70% aqueous methanol and the combined fractions containing rosmarinic acid are evaporated to a volume of about 35 ml. on a rotating evaporator. After the addition of seed crystals of rosmarinic acid, the resulting solution is allowed to stand at +4° C. for 2 to 3 days. The separated crystalline rosmarinic acid is further processed as described in example 1.

Yield: 1.3 g (62% of the theoretical).

What we claim is:

1. Process for the isolation or rosmarinic acid from plants comprising starting from plants or parts of the plants of balmmint (*Melissa officinalis*), extracting the crushed plants or parts of the plants one to three times with 20 to 30 times the amount of water at 80° to 100° C. for 30 to 60 minutes with stirring, acidifying the extract of a pH of 2 to 2.5, thereafter extracting the acidified aqueous extracts with an organic solvent selected from the group consisting of the organic ethers, the higher alkanols immiscible with water and the esters of the aliphatic carboxylic acids, separating the solvent by evaporation, stirring the residue with water at 40° to 80° C. for 20 to 40 minutes, purifying the resulting solution and separating crystalline rosmarinic acid by reducing the volume of the solution and storing the solution at 2° to 8° C.

2. Process according to claim 1 wherein ground balmmint leaves are used as starting material.

3. Process according to claim 1 and 2 wherein diethylether of diisopropylether is used as organic solvent for extraction.

* * * * *